US010781250B2

(12) United States Patent
Somani et al.

(10) Patent No.: US 10,781,250 B2
(45) Date of Patent: Sep. 22, 2020

(54) REFOLDING PROCESS FOR ANTIBODY'S FRAGMENTS

(71) Applicant: Lupin Limited, Mumbai (IN)

(72) Inventors: Sandeep Somani, Pune (IN); Ashish Pandey, Pune (IN); Ashok Mishra, Pune (IN); Rustom Sorab Mody, Pune (IN)

(73) Assignee: Lupin Limited, Mumbai (IN)

( * ) Notice: Subject to any disclaimer, the term of this patent is extended or adjusted under 35 U.S.C. 154(b) by 56 days.

(21) Appl. No.: 15/752,994

(22) PCT Filed: Aug. 17, 2016

(86) PCT No.: PCT/IB2016/054926
§ 371 (c)(1),
(2) Date: Feb. 15, 2018

(87) PCT Pub. No.: WO2017/029620
PCT Pub. Date: Feb. 23, 2017

(65) Prior Publication Data
US 2018/0230206 A1 Aug. 16, 2018

(30) Foreign Application Priority Data
Aug. 17, 2015 (IN) .................. 3118/MUM/2015

(51) Int. Cl.
*C07K 16/22* (2006.01)
*C07K 16/06* (2006.01)

(52) U.S. Cl.
CPC ............ *C07K 16/22* (2013.01); *C07K 16/065* (2013.01); *C07K 2317/10* (2013.01); *C07K 2317/14* (2013.01); *C07K 2317/24* (2013.01); *C07K 2317/522* (2013.01); *C07K 2317/55* (2013.01); *C07K 2317/56* (2013.01)

(58) Field of Classification Search
CPC .. C07K 16/22; C07K 16/065; C07K 2317/10; C07K 2317/14; C07K 2317/522; C07K 2317/56; C07K 2317/24; C07K 2317/55; C12N 15/70; C12N 15/67
See application file for complete search history.

(56) References Cited

U.S. PATENT DOCUMENTS

| | | | |
|---|---|---|---|
| 5,332,671 A | 7/1994 | Ferrara et al. | |
| 2009/0311251 A1* | 12/2009 | Auf Der Maur | A61K 39/39591 424/133.1 |

FOREIGN PATENT DOCUMENTS

| | | | | |
|---|---|---|---|---|
| WO | 2006058890 A2 | 6/2006 | | |
| WO | WO-2014126884 A1 * | 8/2014 | ........... | C07K 1/1133 |
| WO | 2014178078 A2 | 11/2014 | | |
| WO | WO-2014178078 A2 * | 11/2014 | ............ | C07K 16/22 |

OTHER PUBLICATIONS

Lee et al., Protein Expression and Purification 25: 166-173 (Year: 2002).*
Arakawa et al., Antibodies 3: 232-241 (Year: 2014).*
Vallejo et al., Microbial Cell Factories 3: 1-12 (Year: 2004).*
Ferrara et al., Purification and Cloning of Vascular Endothelial Growth Factor Secreted by Pituitary Folliculostellate Cells, Methods in Enzymology, 1991, pp. 391-405, vol. 198.
Houck et al., The Vascular Endothelial Growth Factor Family: Identification of a Fourth Molecular Species and Characterization of Alternative Splicing of RNA, Molecular Endocrinology, 1991, pp. 1806-1814, vol. 5, No. 12.
Kurucz et al., Correct Disulfide Pairing and Efficient Refolding of Detergent-Solubized Single-Chain Fv Proteins from Bacterial Inclusion Bodies, Molecular Immunology, 1995, pp. 1443-1452, vol. 32, No. 17/18.
Leung et al., Vascular Endothelial Growth Factor is a Secreted Angiogenic Mitogen, Science, 1989, pp. 1306-1309, vol. 246.
Xing et al., Prokaryotic expression and renaturation of engineering chimeric Fab antibody against human hepatoma, World Journal of Gastroenterology, 2004, pp. 2029-2033, vol. 10, No. 14.
Arakawa et al., Refolding Technologies for Antibody Fragments, antibodies, May 23, 2014, pp. 232-241, vol. 3, No. 2, MDPI, Basel, Switzerland.
De Bernardez Clark, Refolding of recombinant proteins, Current Opinion in Biotechnology, Biochemical Engineering, 1998, pp. 157-163, Medford, MA, USA.
Fuji et al., Stable Supply of Large Amounts of Human Fab from the Inclusion Bodies in *E. coli*, Journal of Biochemistry, Feb. 2007, pp. 699-707, vol. 141, No. 5, Fukuoka, Japan.
Lee et al., Expression and functional reconstitution of a recombinant antibody (Fab') specific for human apolipoprotein B-100, Journal of Biotechnology, 2003, pp. 189-198, vol. 101, South Korea.
Wibbenmeyer et al., Cloning ,expression, and characterization of the Fab fragment of the anti-lysozyme antibody HyHEL-5, Biochimica et Biophysica Acta, 1999, pp. 191-202, vol. 1430, Bethesda, MD, USA.

* cited by examiner

*Primary Examiner* — Phuong Huynh
(74) *Attorney, Agent, or Firm* — The Webb Law Firm

(57) ABSTRACT

A refolding process of Ranibizumab is disclosed wherein the solubilized solution of heavy chain and/or light chain of Ranibizumab treated with refolding buffer under suitable conditions including pH, temperature and incubation period and the pH and temperature shift is performed at suitable interval to obtain high quality and quantity of refolded protein.

7 Claims, 4 Drawing Sheets

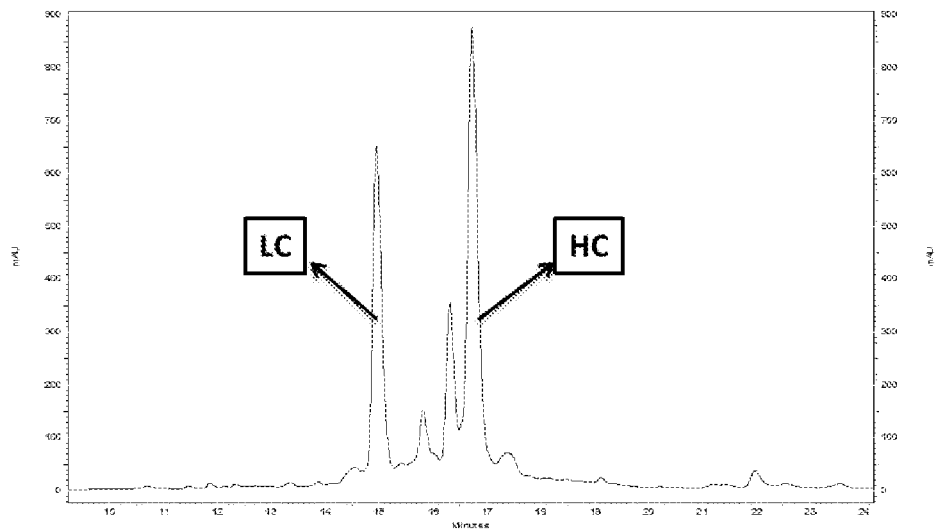
Figure 1: RP-HPLC profile of Solubilized and Reduced IBs
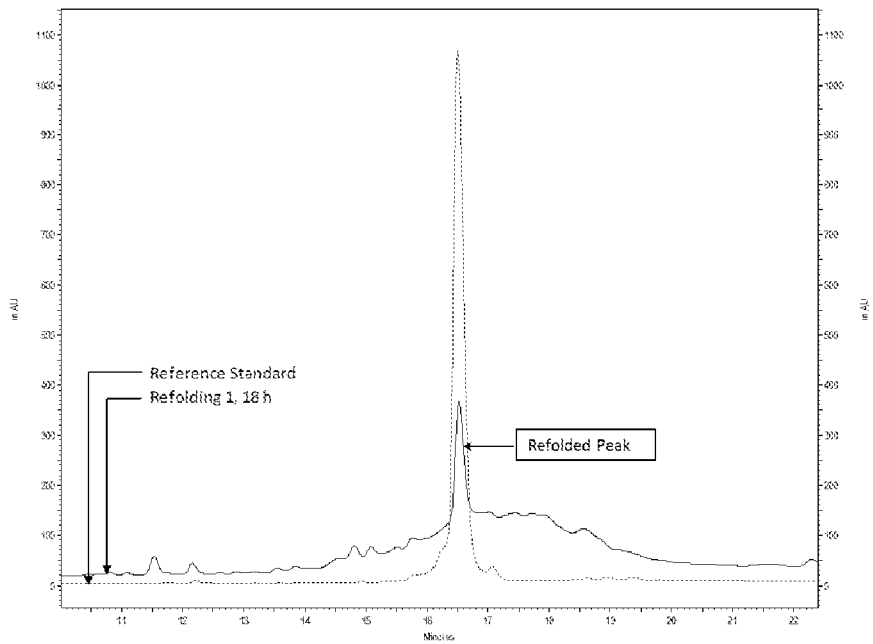
Figure 2: RP-HPLC profile of Refolding 1 at 18 hrs and Reference Standard

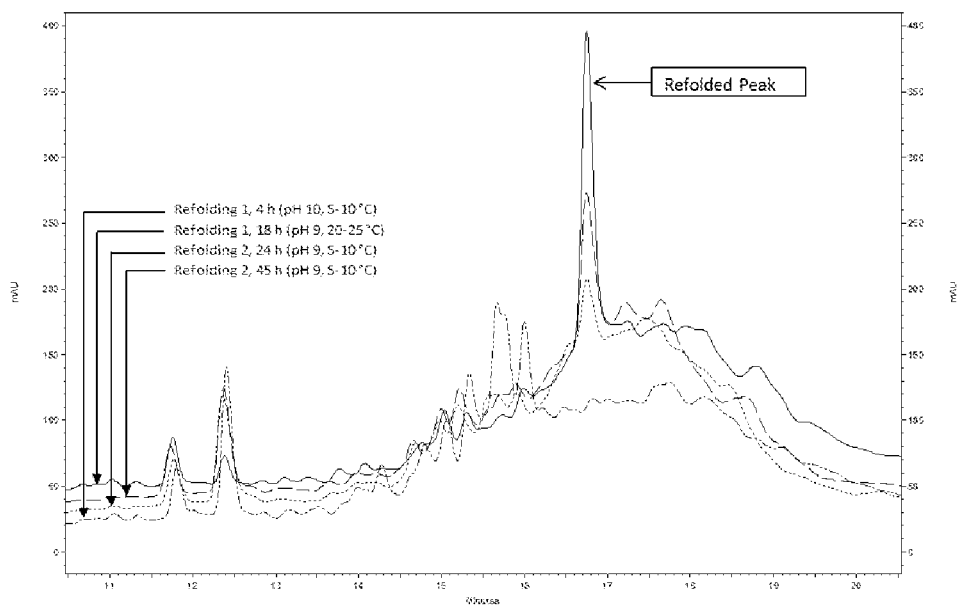
Figure 3: RP-HPLC profile of Refolding 1 and 2 at different time points
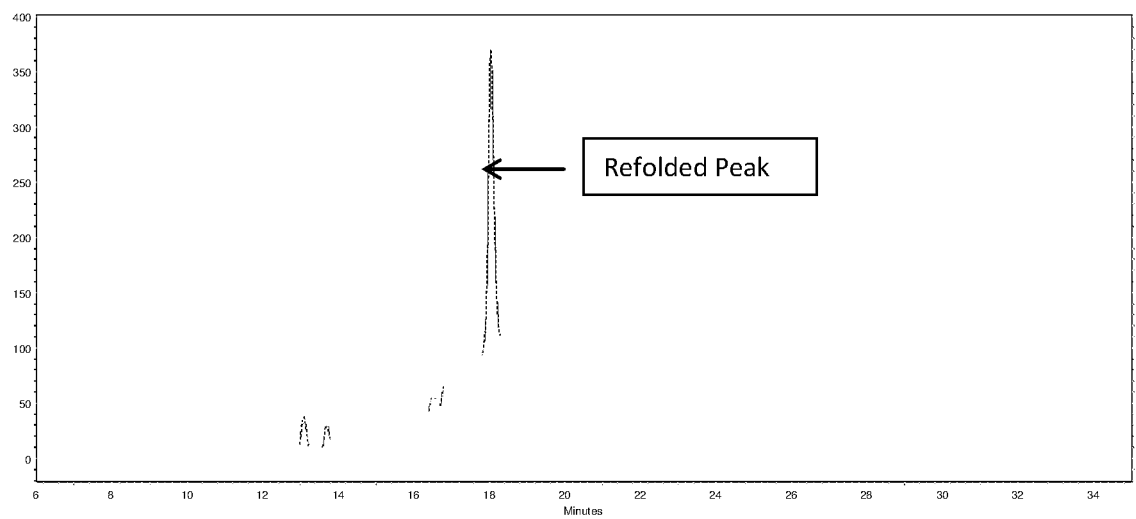
Figure 4: RP-HPLC profile of Refolding

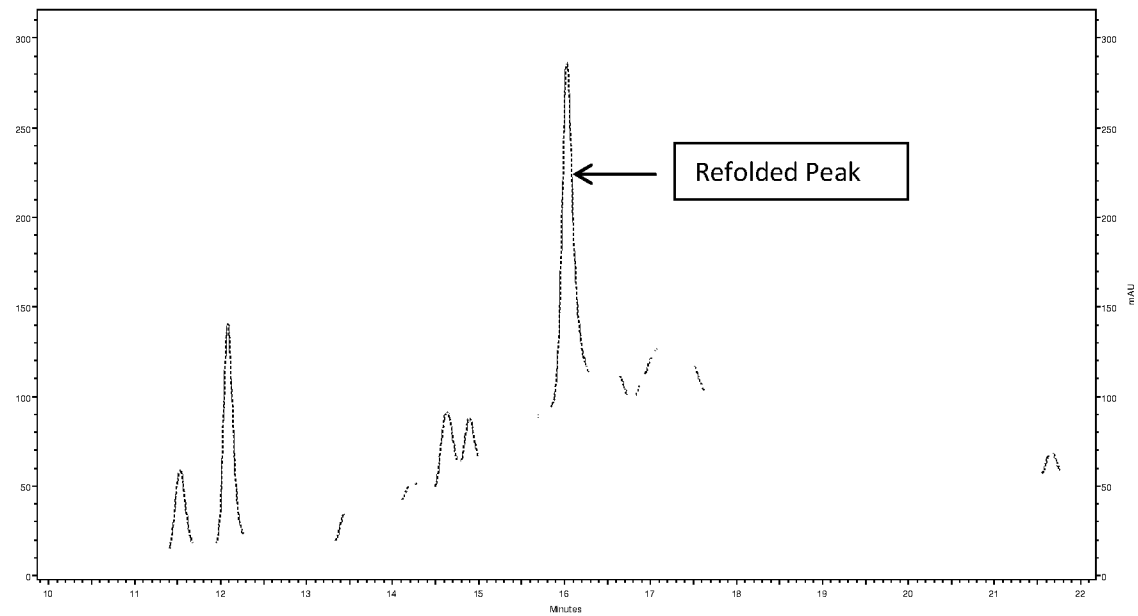
Figure 5: RP-HPLC profile of Refolding, pH of refolding was adjusted to 8.7
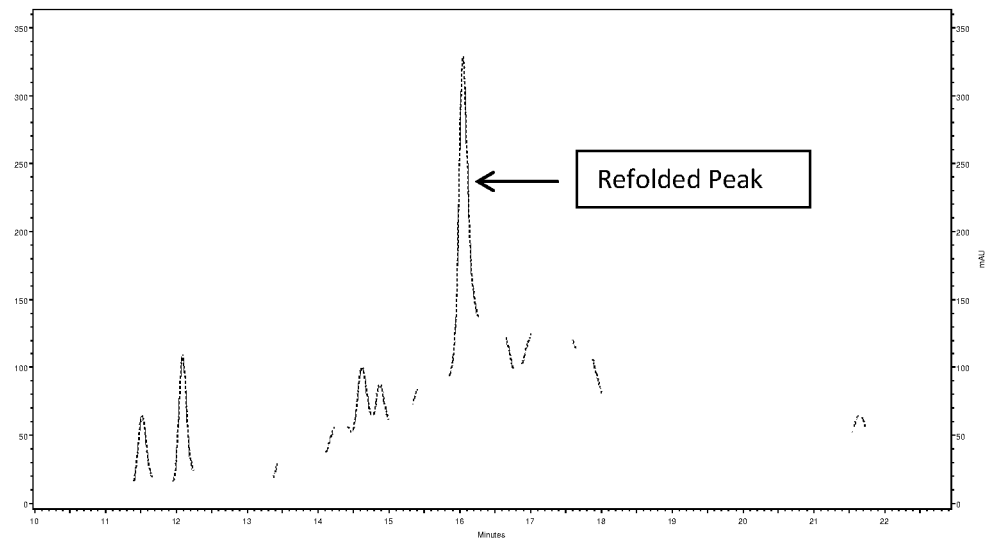
Figure 6: RP-HPLC profile of Refolding, pH of refolding was adjusted to 9.0

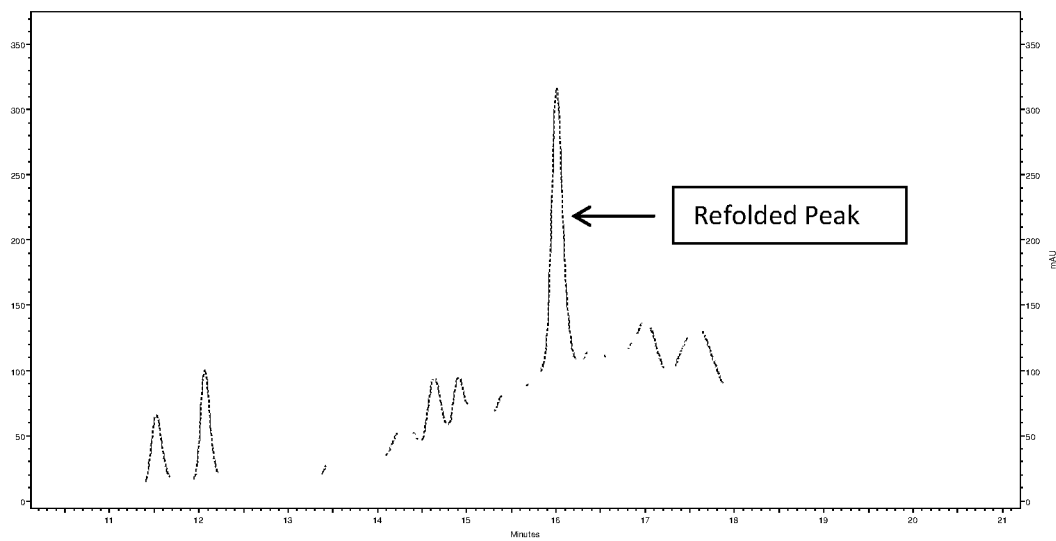
Figure 7: RP-HPLC profile of Refolding, pH of refolding was adjusted to 9.3
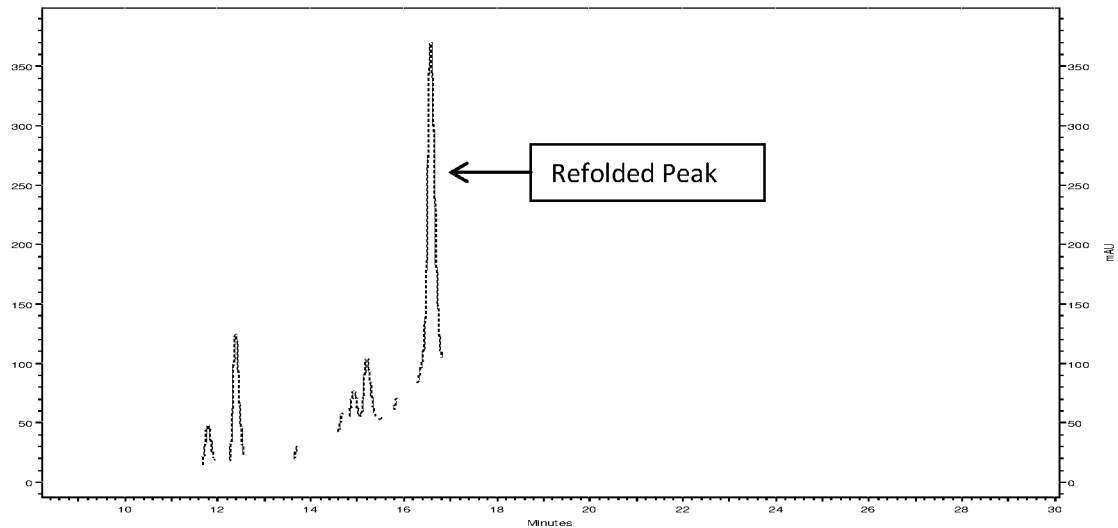
Figure 8: RP-HPLC profile of Refolding

REFOLDING PROCESS FOR ANTIBODY'S FRAGMENTS

CROSS-REFERENCE TO RELATED APPLICATIONS

This application is the United States national phase of International Application No. PCT/IB2016/054926 filed Aug. 17, 2016, and claims priority to Indian Patent Application No. 3118/MUM/2015 filed Aug. 17, 2015, the disclosures of which are hereby incorporated in their entirety by reference.

FIELD OF THE INVENTION

The present invention relates to the process of producing an antibody's fragments such as Ranibizumab. More specifically, the present invention provides a process for recovering refolded Ranibizumab from inclusion bodies formed in bacterial cells.

BACKGROUND OF THE INVENTION

Antibody fragments are smaller than conventional antibodies and generally lack glycosylation, which allows their production in prokaryotic expression systems (Kurucz I et al., *Mol Immunol.* 1995 32(17-18):1443-52). Although gene constructs of these smaller antibody fragments are readily made, expression of folded fragments turns out to be rather difficult due to the non-native structures. Whereas, they can be readily made in bacterial cells as inclusion bodies (IBs) provided it can be successfully refolded. However, the formation of IBs and refolding of the insoluble proteins have been major obstacles in fully utilizing *Escherichia coli* cytoplasmic expression technologies (Tsutomu Arakawa et al., *Antibodies* 2014, 3:232-241).

Ranibizumab (Lucentis) is a recombinant humanized IgG1 kappa isotype monoclonal antibody fragment designed for intraocular use. Ranibizumab binds to and inhibits the biologic activity of human vascular endothelial growth factor A (VEGF-A). Ranibizumab has a molecular weight of approximately 48 kilodaltons as it lacks an Fc region and only consist of Fab therefore it is possible to express it by bacterial expression system, preferably in *E. coli*. Fab fragment correspond to the two identical arms of the antibody molecule, which contain the complete light chains (LC) paired with the VH and CH1 domains of the heavy chains (HC). When the LC and HC domains of Fab are overexpressed in bacterial system either in the same host or separate host, they form insoluble aggregates called as inclusion bodies.

Inclusion bodies contain a mainly inactive misfolded protein in insoluble form and converting it in to an active native confirmation has always been a challenge and several processes have been reported for the recovery of refolded antibody's fragments. (Testuro Fujii et al., *J. Biochem.* 2007 141: 699-707; Jin-Liang Xing et al., *World J Gastroenterol* 2004 10(14): 2029-2033). But some of them are either not scalable at industrial scale and others yield very less refolded protein. Moreover, researches also attempted different techniques of refolding (Eliana De Bernardez Clark, *Current Opinion in Biotechnology* 1998, 9:157-163).

Besides, there is still need in the art to provide a process for recovery of high quality and quantity of refolded protein such as Ranibizumab from inclusion bodies formed in bacterial cell. Therefore the present invention provides an effective process for recovering refolded Ranibizumab from inclusion bodies.

SUMMARY OF THE INVENTION

In an embodiment the invention provides a process for recovering refolded Ranibizumab from the inclusion bodies, the process comprising solubilization and refolding steps carried out under the suitable conditions of pH, temperature and incubation period.

In an embodiment the invention provides solubilized solution of heavy chain and/or light chain of Ranibizumab treated with refolding buffer under suitable conditions including pH, temperature and incubation period wherein the pH and temperature shift is performed at suitable interval to obtain high quality and quantity of refolded protein.

In an embodiment the invention provides a process for recovering refolded Ranibizumab the process comprising the steps of;
  a) isolating a light chain and/or heavy chain of Ranibizumab from the bacterial host cell;
  b) solubilizing said light chain and/or heavy chain of Ranibizumab in a first buffered solution comprising chaotropic agent and/or reducing agent at pH about 9;
  c) refolding said solubilized light chain and heavy chain of Ranibizumab in second buffer solution under suitable conditions having high pH and low temperature till the first incubation period and then shifting the suitable conditions to low pH and high temperature till the second incubation period wherein the pH and temperature shift is performed between the first and second incubation period to obtain refolded Ranibizumab;
  d) recovering said refolded Ranibizumab.

In an embodiment the invention provides a process for recovering a refolded Ranibizumab comprising the steps of:
  a) isolating a light chain and/or heavy chain of Ranibizumab from the bacterial host cell;
  b) solubilizing said light chain and/or heavy chain of Ranibizumab in a first buffered solution comprising chaotropic agent and/or reducing agent at pH selected from about 8 to about 9.5;
  c) refolding said solubilized light chain and heavy chain of Ranibizumab in a second buffered solution comprising a oxidizing agent under suitable conditions having pH selected from about pH 10 to about pH 11, temperature selected from at least about 4° C. to about 12° C. and incubated for a period selected from at least about 4 hours to about 8 hours;
  d) performing a shift in the suitable conditions of step (c) comprising pH selected from about 8 to about 9, temperature selected from at least about 20° C. to about 30° C. and incubated for a period selected from at least about 1 hours to about 20 hours to obtain refolded Ranibizumab; and
  e) recovering said refolded Ranibizumab.

In an embodiment the invention provides a process for recovering a refolded Ranibizumab comprising the steps of:
  a) isolating a light chain and/or heavy chain of Ranibizumab from the bacterial host cell;
  b) solubilizing said light chain and/or heavy chain of Ranibizumab in a first buffered solution comprising chaotropic agent and/or reducing agent at pH selected from about 8 to about 9.5;
  c) refolding said solubilized light chain and heavy chain of Ranibizumab in a second buffered solution comprising a oxidizing agent under suitable conditions having pH selected from about pH 10 to about pH 11, temperature selected from at least about 4° C. to about 12° C. and incubated for a period selected from at least about 4 hours to about 8 hours;

d) performing a shift in the suitable conditions of step (c) comprising pH selected from about 8 to about 9.5, temperature selected from at least about 20° C. to about 30° C. and incubated for a period selected from at least about 1 hours to about 20 hours to obtain refolded Ranibizumab; and e) recovering said refolded Ranibizumab.

In an embodiment the invention provides a process for recovering a refolded Ranibizumab comprising the steps of:

a) isolating a light chain and/or heavy chain of Ranibizumab from the bacterial host cell;

b) solubilizing said light chain and/or heavy chain of Ranibizumab in a first buffered solution comprising chaotropic agent and/or reducing agent at pH about 9;

c) refolding said solubilized light chain and heavy chain of Ranibizumab in a second buffered solution comprising a oxidizing agent under suitable conditions having pH about 10, temperature at least about 5° C. to 10° C. and incubated for at least about 4 hours;

d) performing a shift in the suitable conditions of step (c) comprising pH about 9, temperature at least about 20° C. to 25° C. for an incubation period at least about 14 hours to obtain refolded Ranibizumab; and e) recovering said refolded Ranibizumab.

In an embodiment the invention additionally provides purification process include clarifying the solution containing the Ranibizumab and then contacting said refolded Ranibizumab in the clarified solution with anion exchange and cation exchange column and selectively recovering or eluting the refolded Ranibizumab from each column.

BRIEF DESCRIPTION OF FIGURES

FIG. 1; RP-HPLC profile of Solubilized and Reduced IBs.

FIG. 2; RP-HPLC profile of Refolding 1 at 18 hrs and Reference Standard.

FIG. 3; RP-HPLC profile of Refolding 1 and 2 at different time points.

FIG. 4: RP-HPLC profile of Refolding.

FIG. 5: RP-HPLC profile of Refolding, pH of refolding was adjusted to 8.7

FIG. 6: RP-HPLC profile of Refolding, pH of refolding was adjusted to 9.0

FIG. 7: RP-HPLC profile of Refolding, pH of refolding was adjusted to 9.3

FIG. 8: RP-HPLC profile of Refolding, pH of refolding was adjusted to 9.0

DETAIL DESCRIPTION OF THE INVENTION

Definitions

As used herein, "antibody's fragment" refers generally to proteins having more than about ten amino acids. Antibody fragments are expressed as heterologous protein in to the host cell. Examples of antibody's fragments is Ranibizumab, Abciximab, Anatamomab, Arcitumomab, Bectumomab, Biciromab, Certolizumab, Citatuzumab.bogatox, Naptumomab, Nofetumomab, Sulesomab, Tadocizumab, Telimomab. In preferred embodiment the antibody fragment is Ranibizumab.

As used herein, "vascular endothelial growth factor", or "VEGF", refers to a mammalian growth factor derived originally from bovine pituitary follicular cells having the amino acid sequence disclosed in Castor, C. W., et al., (1991) Methods in Enzymol. 198:391-405, together with functional derivatives thereof having the qualitative biological activity of a corresponding native VEGF, including, but not limited to, the human VEGF amino acid sequence as reported in Houck et al., (1991) Mol. Endocrin. 5:1806-1814. See also, Leung et al. (1989) Science, 246:1306, and, Robinson & Stringer, (2001) Journal of Cell Science, 144 (5):853-865, U.S. Pat. No. 5,332,671. This is also referred to as VEGF-A. As used herein "properly folded" or "biologically active" refers to a molecule with a biologically active conformation and perform desire biological activities.

The terms "purified" or "pure recombinant protein" and the like refer to a material free from substances which normally accompany it as found in its recombinant production and especially in prokaryotic or bacterial cell culture. Thus the terms refer to a recombinant protein which is free of contaminating DNA, host cell proteins or other molecules associated with its in situ environment. The terms refer to a degree of purity that is at least about 75%, at least about 80%, at least about 85%, at least about 90%, at least about 95% or at least about 98% or more.

As used herein, the term "misfolded" protein refers to precipitated or aggregated polypeptides that are contained within inclusion bodies. As used herein, "insoluble" or "misfolded" anti-VEGF antibody such as Ranibizumab or other recombinant protein refers to precipitated or aggregated Ranibizumab or recombinant protein that is contained within the periplasm or intracellular space of prokaryotic host cells and assumes a biologically inactive conformation with mismatched or unformed disulfide bonds. The insoluble recombinant protein is generally, but need not be, contained in inclusion bodies.

As used herein, "chaotropic agent" refers to a compound that, in a suitable concentration in aqueous solution, is capable of changing the spatial configuration or conformation of polypeptides through alterations at the surface thereof so as to render the polypeptide soluble in the aqueous medium. The alterations may occur by changing, e.g., the state of hydration, the solvent environment, or the solvent-surface interaction. The concentration of chaotropic agent will directly affect its strength and effectiveness. A strongly denaturing chaotropic solution contains a chaotropic agent in large concentrations which, in solution, will effectively unfold a polypeptide present in the solution effectively eliminating the proteins secondary structure. The unfolding will be relatively extensive, but reversible. A moderately denaturing chaotropic solution contains a chaotropic agent which, in sufficient concentrations in solution, permits partial folding of a polypeptide from whatever contorted conformation the polypeptide has assumed through intermediates soluble in the solution, into the spatial conformation in which it finds itself when operating in its active form under endogenous or homologous physiological conditions. Examples of chaotropic agents include guanidine hydrochloride, urea, and hydroxides such as sodium or potassium hydroxide. Chaotropic agents include a combination of these reagents, such as a mixture of a hydroxide with urea or guanidine hydrochloride.

As used herein, "reducing agent" refers to a compound that, in a suitable concentration in aqueous solution, maintains free sulfhydryl groups so that the intra- or intermolecular disulfide bonds are chemically disrupted. Representative examples of suitable reducing agents include dithiothreitol (DTT), dithioerythritol (DTE), beta-mercaptoethanol (BME), cysteine, cysteamine, thioglycolate, glutathione, and sodium borohydride.

As used herein, "buffered solution" refers to a solution which resists changes in pH by the action of its acid-base conjugate components.

As used herein, "first buffered solution" refers to a solubilization buffer used for solubilization of inclusion bodies.

As used herein, "second buffered solution" refers to a refolding buffer used for recovering a desire refolded protein confirmation from insoluble misfolded protein.

The invention provides a process for recovering and purifying refolded recombinant proteins from bacterial host cell. The processes of the invention are broadly applicable to antibody fragments like Fab, ScFv which includes but not limited to Ranibizumab, Abciximab, Anatamomab, Arcitumomab, Bectumomab, Biciromab, Certolizumab, Citatuzumab.bogatox, Naptumomab, Nofetumomab, Sulesomab, Tadocizumab, Telimomab. In preferred embodiment the antibody fragment is Ranibizumab.

The present invention provides a process for recovery of refolded protein from insoluble protein formed in intracellular or in the periplasmic space bacterial host cell. In one embodiment, Inclusion bodies are isolated from the prokaryotic cell as per the process known in the art. Isolated inclusion bodies mainly comprise misfolded insoluble proteins and impurities. In certain embodiments, the processes and procedures are applicable to manufacturing or industrial scale production, refolding, and purification of the recombinant protein.

In one embodiment, the isolated IBs comprising heavy chain and/or light chain of Ranibizumab in the pellet and then incubated in a first buffered solution sufficient to substantially solubilize the IBs. This incubation takes place under suitable conditions of concentration, incubation time, and incubation temperature that will allow solubilization of desired amount or substantially all the IBs. In such embodiment reduction is carried out with suitable reducing agent for about 30 minutes to 45 minutes and thereafter reduced solution is filtered and further used for refolding.

In embodiment the first buffer comprises Tris-Cl, Urea. In certain embodiment the Tris-Cl is present in concentration selected from 10 mM to 60 mM, preferably 50 mM. In certain embodiment urea is present in concentration selected from 6M to 8M, preferably 8 M. In embodiment the pH of the first buffer solution is selected from 8.5 to 10, preferably 9.

In an embodiment the chaotropic agents are selected from guanidine hydrochloride, urea, and hydroxides such as sodium or potassium hydroxide.

In embodiment the reducing agent is selected from dithiothreitol (DTT), dithioerythritol (DTE), beta-mercaptoethanol (BME), cysteine, cysteamine, thioglycolate, glutathione, and sodium borohydride.

In an embodiment, solubilized heavy and/or light chain of Ranibizumab is further treated with second buffer solution or refolding buffer to perform refolding. Second buffer solution comprising suitable conditions having high pH and low temperature till the first incubation period and then maintain suitable conditions having low pH and high temperature till the second incubation period wherein the pH and temperature shift is performed between the first and second incubation period.

In an embodiment the solubilized heavy and/or light chain of Ranibizumab solution is treated with second buffered solution under suitable conditions having pH selected from about pH 10 to about pH 11, temperature selected from at least about 4° C. to about 12° C. and incubated for a period selected from at least about 4 hours to about 8 hours then pH and temperature shift is performed to pH selected from about 8 to about 9, temperature selected from at least about 20° C. to about 30° C. and incubated for a period selected from at least about 14 hours to about 20 hours. In such embodiment, pH shift means shifting the pH from pH 10 to 11 to pH 8 to 9. In certain embodiment, pH shift means shifting the pH from pH 10 to 11 to pH 8 to 9.5. Temperature shift means shifting temperature from 4° C. to 12° C. to 20° C. to 30° C.

In certain embodiment the first incubation period is selected from about 1 hour to about 25 hours. In preferred embodiment the first incubation period is selected from about 4 hour to about 15 hours. In preferred embodiment the first incubation period is about 4 hour.

In certain embodiment the second incubation period is selected from about 1 hour to about 25 hours. In preferred embodiment the first incubation period is selected from about 12 hour to about 25 hours. In preferred embodiment the first incubation period is about 14 hour.

In embodiment the second buffer comprises Tris, Arginine and sorbitol. In certain embodiment the Tris is present in concentration selected from 10 mM to 60 mM, preferably 50 mM. In certain embodiment arginine is present in concentration selected from 0.1M to 1M, preferably 0.6 mM. In certain embodiment sorbitol is present in concentration selected from 1% to 8%, preferably 5%.

In certain embodiment the second buffer comprises oxidizing agent concentration is selected from 1 mM to 10 mM. In an embodiment oxidizing agent concentration is 3 mM. In certain embodiment oxidizing agent is selected from cystine, oxidized glutathione (GSSG), copper sulfate, dehydroascorbate, sodium thiosulfate. In an embodiment the oxidizing agent is cystine.

In an embodiment the invention provides a process for recovering refolded Ranibizumab the process comprising the steps of;
  a) isolating a light chain and/or heavy chain of Ranibizumab from the bacterial host cell;
  b) solubilizing said light chain and/or heavy chain of Ranibizumab in a first buffered solution comprising chaotropic agent and/or reducing agent at pH about 9;
  c) refolding said solubilized light chain and heavy chain of Ranibizumab in second buffer solution under suitable conditions having high pH and low temperature till the first incubation period and then shifting the suitable conditions to low pH and high temperature till the second incubation period wherein the pH and temperature shift is performed between the first and second incubation period to obtain refolded Ranibizumab;
  d) recovering said refolded Ranibizumab.

In an embodiment the invention provides a process for recovering a refolded Ranibizumab comprising the steps of:
  a) isolating a light chain and/or heavy chain of Ranibizumab from the bacterial host cell;
  b) solubilizing said light chain and/or heavy chain of Ranibizumab in a first buffered solution comprising chaotropic agent and/or reducing agent at pH selected from about 8 to about 9.5;
  c) refolding said solubilized light chain and heavy chain of Ranibizumab in a second buffered solution comprising a oxidizing agent under suitable conditions having pH selected from about pH 10 to about pH11, temperature selected from at least about 4° C. to about 12° C. and incubated for a period selected from at least about 4 hours to about 8 hours;

d) performing a shift in the suitable conditions of step (c) comprising pH selected from about 8 to about 9, temperature selected from at least about 20° C. to about 30° C. and incubated for a period selected from at least about 1 hours to about 20 hours to obtain refolded Ranibizumab; and e) recovering said refolded Ranibizumab.

In an embodiment the invention provides a process for recovering a refolded Ranibizumab comprising the steps of:

a) isolating a light chain and/or heavy chain of Ranibizumab from the bacterial host cell;

b) solubilizing said light chain and/or heavy chain of Ranibizumab in a first buffered solution comprising chaotropic agent and/or reducing agent at pH selected from about 8 to about 9.5;

c) refolding said solubilized light chain and heavy chain of Ranibizumab in a second buffered solution comprising a oxidizing agent under suitable conditions having pH selected from about pH 10 to about pH11, temperature selected from at least about 4° C. to about 12° C. and incubated for a period selected from at least about 1 hours to about 25 hours;

d) performing a shift in the suitable conditions of step (c) comprising pH selected from about 8 to about 9.5, temperature selected from at least about 20° C. to about 30° C. and incubated for a period selected from at least about 1 hours to about 25 hours to obtain refolded Ranibizumab; and e) recovering said refolded Ranibizumab.

In an embodiment the invention provides a process for recovering a refolded Ranibizumab comprising the steps of:

a) isolating a light chain and/or heavy chain of Ranibizumab from the bacterial host cell;

b) solubilizing said light chain and/or heavy chain of Ranibizumab in a first buffered solution comprising chaotropic agent and/or reducing agent at pH selected from about 8 to about 9.5;

c) refolding said solubilized light chain and heavy chain of Ranibizumab in a second buffered solution comprising a oxidizing agent under suitable conditions having pH selected from about pH 10 to about pH11, temperature selected from at least about 4° C. to about 12° C. and incubated for a period selected from at least about 4 hours to about 8 hours;

d) performing a shift in the suitable conditions of step (c) comprising pH selected from about 8 to about 9.5, temperature selected from at least about 20° C. to about 30° C. and incubated for a period selected from at least about 1 hours to about 20 hours to obtain refolded Ranibizumab; and e) recovering said refolded Ranibizumab.

In an embodiment the invention provides a process for recovering a refolded Ranibizumab comprising the steps of:

a) isolating a light chain and/or heavy chain of Ranibizumab from the bacterial host cell;

b) solubilizing said light chain and/or heavy chain of Ranibizumab in a first buffered solution comprising chaotropic agent and/or reducing agent at pH about 9;

c) refolding said solubilized light chain and heavy chain of Ranibizumab in a second buffered solution comprising a oxidizing agent under suitable conditions having pH about 10, temperature at least about 5° C. to 10° C. and incubated for at least about 4 hours;

d) performing a shift in the suitable conditions of step (c) comprising pH about 9, temperature at least about 20° C. to 25° C. for an incubation period at least about 14 hours to obtain refolded Ranibizumab; and e) recovering said refolded Ranibizumab.

In embodiment the refolded Ranibizumab is purified by using suitable chromatography methods. In preferred embodiment the refolded Ranibizumab is filtered and then subjected to anion exchange column and cation exchange column.

In an embodiment, the purification process of refolded Ranibizumab comprises one or more impurities, wherein the method comprises:

(a) first anion exchange chromatography;
(b) second anion exchange chromatography; and
(c) cation exchange chromatography;
(d) Optionally filtration can be performed either before the step (a) or step (c).

In an embodiment, the purification process of refolded Ranibizumab comprises one or more impurities, wherein the method comprises:

(a) loading the composition comprising refolded Ranibizumab and one or more impurities on to a first anion exchange chromatography column equilibrated with an equilibration buffer having pH from about 8 to about 10 and eluting the column with an elution buffer having pH from about 7 to about 9 to obtain a first elution solution;

(b) loading the first elution solution obtained from step (a) on to a second anion exchange chromatography column equilibrated with an equilibration buffer having pH from about 8 to about 10 and eluting the column with an elution buffer having pH from about 7 to about 10 to obtain second elution solution; and (c) loading the second elution solution obtained from step (b) on to a cation exchange chromatography column equilibrated with an equilibration buffer having pH from about 4 to about 6.5 and eluting the bound Ranibizumab using salt gradient In an embodiment, the purification process of refolded Ranibizumab comprises one or more impurities, wherein the method comprises:

(a) loading the composition comprising Ranibizumab and one or more impurities on to a first anion exchange chromatography column equilibrated with an equilibration buffer having pH from about 8.5 to about 9.5 and eluting the column with an elution buffer having pH from about 7.5 to about 8.5 to obtain a first elution solution;

(b) loading the first elution solution obtained from step (a) on to a second anion exchange chromatography column equilibrated with an equilibration buffer having pH from about 8.5 to about 9.5 and eluting the column with an elution buffer having pH from about 7.5 to about 8.5 to obtain second elution solution; and (c) loading the second elution solution obtained from step (b) on to a cation exchange chromatography column equilibrated with an equilibration buffer having pH from about 4.5 to about 6.0 and eluting the column with an elution buffer having pH from about 4.5 to about 6.0 to obtain purified antibody of interest;

(d) Optionally filtration can be performed either before the step (a) or step (c).

The invention may be illustrated by way of examples below, those having ordinary skill in the art will clearly understand that many modifications are possible in the embodiments and examples without departing from the teachings thereof.

Example 1

36 g Inclusion bodies (IBs) obtained after fermentation, harvesting and IBs isolation-were solubilized in around 720 mL of first buffer comprised of 8 M Urea, 50 mM Tris at pH 9 and reduction was done using 4 mM DTT for 45 minutes. The solubilized and reduced IBs were then filtered with 0.8+0.2 μm filter.

The profile of solubilized IBs was checked through RP-HPLC as shown in FIG. 1. The heavy chain and light chain peaks can be observed in the profile.

Around 360 ml of solubilized and reduced IBs solution was then added to around 8640 mL of refolding buffer comprised of 0.6 M Arginine, 5% sorbitol and 50 mM Tris at pH 10 and temperature of 5-10° C. within 1 h at constant flow rate. Refolding at this pH was carried out for 4 h and then the pH of the refolding solution was adjusted to 9 with an acid. The temperature was also increased to 20-25° C. after pH adjustment. Refolding was continued for further 14 hrs. The RP-HPLC profile is shown in FIG. 2 and FIG. 3 which is referred as Refolding 1. The refolded Fab peak can be observed in the profile.

Example 2

21.5 g Inclusion bodies (IBs) obtained after fermentation, harvesting and IBs isolation were solubilized in around 430 ml of first buffer comprised of 8 M Urea, 50 mM Tris at pH 9 and reduction was done using 4 mM DTT for 45 minutes. The solubilized and reduced IBs were then filtered with 0.8+0.2 μm filter.

Around 400 ml of solubilized and reduced IBs was used and it was added to around 9.5 L of refolding buffer comprised of 0.6 M Arginine, 5% sorbitol, 50 mM Tris which was at pH 9 and temperature of 5-10° C. within 1 hr at constant flow rate. The refolding was carried out for around 45 h. This refolding is referred as Refolding 2. The purity of refolded protein obtained at 24 hours is 8.1% and yield of refolded protein obtained at 24 hours is 3.1%. The RP-HPLC profile is shown in FIGS. 2 and 3 and referred as Refolding 2. Thus, from the RP-HPLC results it was observed that Refolding 1 was giving higher refolding in 18 h compared to Refolding 2 for 45 h.

Example 3

100 g Inclusion bodies obtained after fermentation, harvesting and IB washing were solubilized in 1500 ml of solubilization buffer (8 M Urea, 50 mM Tris pH 9) and reduction was done using 4 mM DTT for 45 minutes. The solubilized and reduced IBs were then filtered.

800 ml of solubilized and reduced IBs was added to ~19 L of refolding buffer (0.6 M Arginine, 5% sorbitol, 50 mM Tris, pH 10) at 5-10° C. within 1 h at constant flow rate. The refolding at this condition was continued for around 4 to 5 h. After that three aliquot (2 L each) were removed from the 19 L refolding solution and pH of each aliquots was adjusted to 8.7, 9.0, and 9.3 respectively with 6 N HCl and refolding at this condition was continued up to 21 to 28 hours at temperature of 21 to 25° C. RP-HPLC profile of Refolding at different pH is shown in FIG. 5 to FIG. 7. The profile shows that refolding within the studied pH range gives almost similar refolding.

Example 4

Around 1.6 Kg Inclusion bodies obtained after fermentation, harvesting and IB washing were solubilized in ~32 L of solubilization buffer (8 M Urea, 50 mM Tris pH 9) and reduction was done using DTT. The solubilized and reduced IBs were then filtered.

Solubilized and reduced IBs were added to around 800 L of refolding buffer (0.6 M Arginine, 5% sorbitol, 50 mM Tris, pH 10.1) at 5-10° C. within 1 hr at constant flow rate. The refolding at this condition was continued for around 4 to 5 h and pH of refolding was adjusted to 9.1 with 6 N HCl. Refolding temperature was increased to 21-25° C. and refolding was continued up to 21-22 h. RP-HPLC profile of refolding is shown in FIG. 4. The purity and yield of refolded protein is 47.3% and 13.6% respectively.

Example 5

45 g Inclusion bodies obtained after fermentation, harvesting and IB washing were solubilized in 900 ml of solubilization buffer (8 M Urea, 50 mM Tris pH 9) and reduction was done using 4 mM DTT for 45 minutes. The solubilized and reduced IBs were then filtered.

400 ml of solubilized and reduced IBs was added to around 9.5 L of refolding buffer (0.6 M Arginine, 5% sorbitol, 50 mM Tris) at 5-10° C. within 1 h at constant flow rate, pH of refolding buffer was approximately 10.5 to 10.6. The refolding at this condition was continued for around 4 to 5 h and then pH of refolding solution was adjusted to 9 with 6 N HCl. Refolding temperature was increased to 21-25° C. and refolding was continued up to 21-22 h. The RP-HPLC profile of refolding is shown in FIG. 8.

The invention claimed is:

1. A process for recovering refolded Ranibizumab, the process comprising the steps of;
   a) isolating a light chain and heavy chain of Ranibizumab from a bacterial host cell;
   b) solubilizing said light chain and heavy chain of Ranibizumab in a first buffer solution comprising about 8 M urea, about 50 mM Tris, and about 4 mM DTT at a pH of about 8.5 to about 10;
   c) refolding the solubilized light chain and heavy chain of Ranibizumab in a second buffer solution comprising about 0.6 M Arginine, about 5% sorbitol, and about 50 mM Tris in a first incubation period under a pH from about 10 to about 11 and a temperature from about 4° C. to about 12° C. and then shifting the second buffer solution to a pH of about 8.7 to about 9.3 pH and a temperature of about 20° C. to about 25° C. in a second incubation period to obtain refolded Ranibizumab; and
   d) recovering said refolded Ranibizumab.

2. The process as claimed in claim 1, wherein the second buffer solution of step (c) maintains pH 10 during the first incubation period.

3. The process as claimed in claim 1, wherein the second buffer solution of step (c) maintains a temperature from about 5° C. to about 10° C. during the first incubation period.

4. The process as claimed in claim 1, wherein the first incubation period is 4 hours.

5. The process as claimed in claim 1, wherein the second buffer solution of step (c) maintains a pH of 9 during the second incubation period.

6. The process as claimed in claim 1, wherein the second incubation period is 14 hours.

7. The process as claimed in claim 1, wherein the recovered refolded Ranibizumab is further purified by using at least one purification method comprising filtration and anion chromatography or filtration and cation chromatography.

* * * * *